United States Patent [19]
Bennett et al.

[11] Patent Number: 5,431,679
[45] Date of Patent: Jul. 11, 1995

[54] ABSORBABLE BLOCK COPOLYMERS AND SURGICAL ARTICLES FABRICATED THEREFROM

[75] Inventors: Steven L. Bennett, New Haven; Cheng-Kung Liu, Norwalk, both of Conn.

[73] Assignee: United States Surgical Corporation, Norwalk, Conn.

[21] Appl. No.: 209,330

[22] Filed: Mar. 10, 1994

[51] Int. Cl.⁶ .................. A61L 17/00; C08G 63/06; C08G 63/64

[52] U.S. Cl. .................. 606/230; 606/77; 606/157; 606/219; 525/411; 525/413; 525/415

[58] Field of Search .................. 525/411, 413, 415; 606/230, 77, 157, 219

[56] References Cited

U.S. PATENT DOCUMENTS

| | | |
|---|---|---|
| 2,668,162 | 2/1954 | Lowe . |
| 2,683,136 | 7/1954 | Higgins . |
| 2,703,316 | 3/1955 | Schneider . |
| 2,758,987 | 8/1956 | Salzberg . |
| 3,225,766 | 12/1986 | Baptist et al. . |
| 3,268,486 | 8/1966 | Klootwijk . |
| 3,268,487 | 8/1966 | Klootwijk . |
| 3,297,033 | 1/1967 | Schmitt et al. . |
| 3,422,181 | 1/1969 | Chirqwin, Jr. . |
| 3,422,871 | 5/1969 | Schmitt et al. . |
| 3,463,158 | 8/1969 | Schmitt et al. . |
| 3,468,853 | 9/1969 | Schmitt et al. . |
| 3,531,561 | 9/1970 | Trehu . |
| 3,565,869 | 2/1971 | DeProspero . |
| 3,597,449 | 8/1971 | DeProspero et al. . |
| 3,620,218 | 11/1971 | Schmitt et al. . |
| 3,626,948 | 12/1971 | Glick et al. . |
| 3,636,956 | 1/1972 | Schneider . |
| 3,733,919 | 5/1973 | Rupp, II . |
| 3,736,646 | 6/1973 | Schmitt et al. . |
| 3,739,773 | 6/1973 | Schmitt et al. . |
| 3,772,420 | 11/1973 | Glick et al. . |
| 3,781,349 | 12/1993 | Ramsey et al. . |
| 3,784,585 | 1/1974 | Schmitt et al. . |
| 3,792,010 | 2/1974 | Wasserman et al. . |
| 3,797,499 | 3/1974 | Schneider . |
| 3,839,297 | 10/1974 | Wasserman et al. . |
| 3,846,382 | 11/1974 | Ramsey et al. . |
| 3,867,190 | 2/1975 | Schmitt et al. . |
| 3,878,284 | 4/1975 | Schmitt et al. .............. 264/331 |
| 3,896,802 | 7/1975 | Williams .............. 128/149 |
| 3,902,497 | 9/1975 | Casey .............. 128/290 |
| 3,937,223 | 2/1976 | Roth .............. 128/335 |
| 3,982,543 | 9/1976 | Schmitt et al. .............. 428/394 |
| 3,987,937 | 10/1976 | Coucher .............. 222/193 |
| 4,033,938 | 7/1977 | August et al. . |
| 4,045,418 | 8/1977 | Sinclair .............. 156/327 |
| 4,057,537 | 11/1977 | Sinclair .............. 260/78.3 R |
| 4,060,089 | 11/1977 | Noiles .............. 128/325 |
| 4,137,921 | 2/1979 | Okuzumi et al. .............. 528/354 |
| 4,157,437 | 6/1979 | Okuzumi et al. .............. 528/354 |
| 4,243,775 | 1/1981 | Kosensaft et al. .............. 525/415 |
| 4,246,904 | 1/1981 | Kaplan .............. 525/444 |
| 4,273,920 | 6/1981 | Nevin .............. 528/361 |

(List continued on next page.)

FOREIGN PATENT DOCUMENTS

| | | |
|---|---|---|
| 779291 | 7/1957 | United Kingdom . |
| 1332505 | 10/1973 | United Kingdom . |
| 1414600 | 11/1975 | United Kingdom . |
| 2102827 | 2/1983 | United Kingdom . |

OTHER PUBLICATIONS

D. K. Gilding et al., "Biodegradable Polymers for Use in Surgery-Polyglycolic/Poly(lactic) acid homo-and copolymers: 1," Polymer, vol. 20, pp. 1459–1464 (1979).
D. F. Williams (ed.) Biocompatability of Clinical Implant Materials, vol. II, Chapter 9: "Biodegradable Polymers" (1981).

*Primary Examiner*—David Buttner

[57] ABSTRACT

Block copolymers wherein one of the blocks is made from hard phase forming monomers and another of the blocks is made from soft phase forming monomers co-polymerized with randomly intermingled units of other soft phase forming monomers. The copolymers are useful in forming surgical articles, including both monofilament and multifilament sutures.

11 Claims, 1 Drawing Sheet

U.S. PATENT DOCUMENTS

| | | | |
|---|---|---|---|
| 4,275,813 | 6/1981 | Noiles | 206/339 |
| 4,279,249 | 7/1981 | Vert et al. | 525/415 |
| 4,300,565 | 11/1981 | Rosensaft et al. | 528/354 |
| 4,429,080 | 1/1984 | Casey et al. | 525/415 |
| 4,605,730 | 8/1986 | Shalaby et al. | 528/357 |
| 4,705,820 | 11/1987 | Wang et al. | 524/381 |
| 4,744,365 | 5/1988 | Kaplan et al. | 528/354 |
| 4,788,979 | 12/1988 | Jarrett et al. | 528/354 |
| 4,791,929 | 12/1988 | Jarrett et al. | 528/354 |
| 4,891,263 | 1/1990 | Kotliar et al. | 528/354 |
| 4,916,193 | 4/1990 | Tang et al. | 525/413 |
| 4,916,207 | 4/1990 | Boyle, Jr. et al. | 528/370 |
| 4,920,203 | 4/1990 | Tang et al. | 525/409 |
| 5,066,772 | 11/1991 | Tang et al. | 525/409 |
| 5,080,665 | 1/1992 | Jarrett et al. | 525/415 |
| 5,120,802 | 6/1992 | Mares et al. | 525/415 |
| 5,133,739 | 7/1992 | Bezwada et al. | 528/357 |
| 5,145,945 | 9/1992 | Tang et al. | 528/370 |
| 5,152,781 | 10/1992 | Tang et al. | 528/354 |
| 5,185,408 | 2/1993 | Tang et al. | 525/415 |
| 5,225,520 | 7/1993 | Kennedy et al. | 525/415 |
| 5,236,444 | 8/1993 | Muth et al. | 606/230 |
| 5,252,701 | 10/1993 | Jarrett et al. | 525/415 |
| 5,314,989 | 5/1994 | Kennedy et al. | 525/415 |
| 5,322,925 | 6/1994 | Muth et al. | 525/415 |

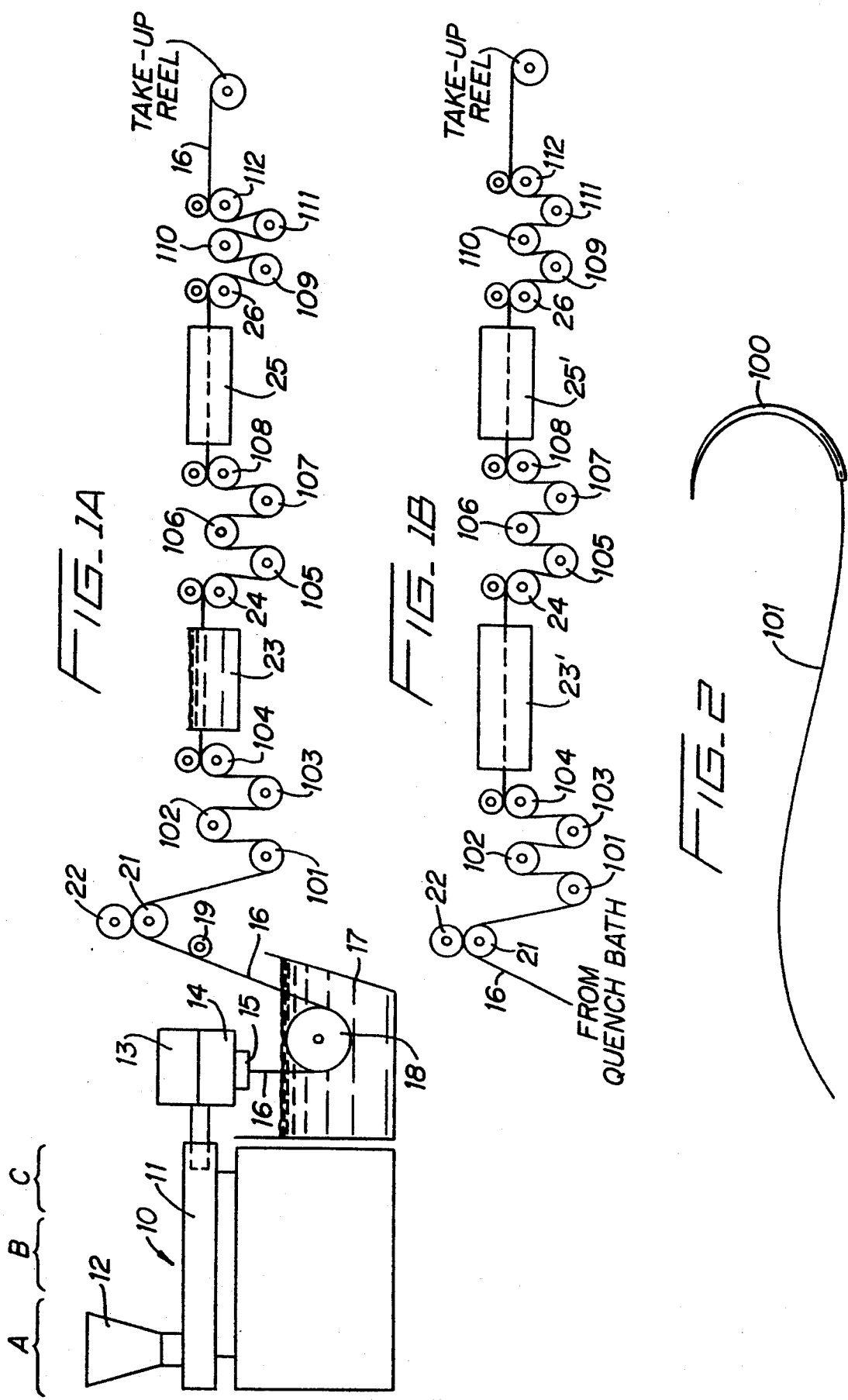

ABSORBABLE BLOCK COPOLYMERS AND SURGICAL ARTICLES FABRICATED THEREFROM

TECHNICAL FIELD

The present invention relates to absorbable block copolymers having one of the blocks made from hard phase forming monomers and another of said blocks made from randomly copolymerized soft phase forming monomers, and more particularly to surgical articles made totally or in part therefrom, including both monofilament and multifilament sutures.

BACKGROUND OF THE INVENTION

Polymers and copolymers of, and surgical devices made from lactide and/or glycolide and/or related compounds are well-know. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D. K. Gilding et al., "Biodegradable polymers for use in surgery-polyglycolic/poly (lactic acid) homo-and copolymers: 1," *Polymer,* Volume 20, pages 1459–1464 (1979), and D. F. Williams (ed.) *Biocompatibility Of Clinical Implant Materials,* Volume II, chapter 9: "Biodegradable Polymers" (1981).

Surgical devices prepared from copolymers containing lactide or glycolide and trimethylene carbonate have been described.

U.S. Pat. No. 4,429,080 describes glycolide end blocks and glycolide trimethylene carbonate random copolymer middle blocks. The block copolymers described in the '080 patent contain no 1,4 dioxane-2-one.

As another example, U.S. Pat. No. 5,066,772 describes random copolymers of lactide and trimethylene carbonate and triblock copolymers having lactide end blocks and lactide-trimethylene carbonate random copolymer center blocks. The block copolymers of the '772 patent do not include a block which has predominantly glycolic acid ester linkages.

Block copolymers described in U.S. Pat. No. 5,145,945 do not include a block having random copolymers of trimethylene carbonate and caprolactone nor do they include a block which is predominantly glycolide. In addition, see U.S. Pat. Nos. 4,243,775; 4,300,565; 4,705,820; 4,891,263; 4,916,193; 4,902,203.

The present invention provides another bioabsorbable copolymer useful in the preparation of surgical articles such as sutures which exhibit desirable physical characteristics, such as knot pull strength and straight pull strength.

SUMMARY OF THE INVENTION

It has now been found that absorbable surgical articles may be formed from a block copolymer having one of the blocks made from hard phase forming monomers and another of the blocks made from random copolymers of soft phase forming monomers. Hard phase forming monomers include glycolide and lactide while soft phase forming monomers include 1,4 dioxane-2-one and 1,3 dioxane-2-one and caprolactone.

Preferably, block copolymers useful in forming surgical articles in accordance with the present invention include block copolymers comprising one block having glycolic acid ester units as a predominant component thereof. A "predominant component" is a component which is present is an amount greater than 50 percent.

In a particularly useful embodiment the block copolymers of the present invention may be spun into fibers. The fibers can be fabricated into both monofilament and braided multifilament sutures.

In another aspect of the present invention there is provided a process for manufacturing a suture exhibiting excellent energy and/or increased knot performance for a given size comprising the operations of extruding the block copolymer of the present invention at an extrusion temperature of from about 180° C. to about 245° C. to provide a monofilament fiber, stretching the solidified monofilament at a temperature of from about 30° C. to about 95° C. in water (or other suitable liquid medium) or at from about 40° C. to about 120° C. in air (or other suitable gaseous medium) at a stretch ratio of from about 3:1 to about 10:1 to provide a stretched monofilament. The stretched monofilament preferably is then frozen at a temperature of from about −15° C. to about 0° C. The suture then may be annealed with or without relaxation at a temperature of from about 80° C. to about 130° C. to provide the finished suture.

BRIEF DESCRIPTION OF THE DRAWINGS

FIG. 1A is a schematic illustration of an apparatus which is suitable for manufacturing the monofilament suture of this invention; and, FIG. 1B is a modification of the apparatus of FIG. 1A which is particularly suitable for manufacturing the monofilament sutures of the present invention of smaller size, e.g., sizes 4/0 and smaller.

FIG. 2 is a perspective view of a suture of the present invention attached to a needle.

DESCRIPTION OF THE PREFERRED EMBODIMENTS

In accordance with the present invention, it has been found that a block copolymer having two specific types of blocks, an "A" block having a proportion of glycolic acid ester units as the predominant component thereof and a "B" block comprising 1,3 dioxane-2-one randomly copolymerized with caprolactone, preferrably epsilon-caprolcatone, can advantageously be combined to form a block copolymer useful in forming surgical elements.

The block copolymer compositions of the present invention include an A block formed from a copolymer which has glycolide as the predominant component thereof. That is, glycolide comprises at least 50 mole percent of the first block. Preferably, glycolide comprises at least about 60 mole percent of the first block. Most preferably, the first block is a glycolide homopolymer. The glycolide may be copolymerized with any monomer which provides an absorbable copolymer to form the A block. Such monomers include but are not limited to lactide, trimethylene carbonate, p-dioxanone, and epsilon-caprolactone. The copolymers of glycolide which form the first block can be random or block copolymers and can be synthesized by known methods.

See, for example. U.S. Pat. Nos. 4,653,497; 4,838,267; 4,429,080; 4,605,730; and 4,788,979 the disclosures of which are incorporated herein by reference.

The B block of the composition of this invention has epsilone-caprolactone and 1,3 dioxane-2-one linkages. Preferably epsilone-caprolactone comprises from about 20 mole percent to about 80 mole percent, and more preferrably from about 25 mole percent to about 50 mole percent of the B block. Most preferably, epsilone-caprolactone comprises at least about 30 mole percent of the B block, the remainder of the block comprising 1,3 dioxane-2-one. For purposes of the present invention, copolymers of 1,3 dioxane-2-one and epsilon-caprolactone having an inherent viscosity of from about 1.0 to about 1.5 dl/g measured at 30° C. and a concentration of 0.25 g/dl in chloroform may generally be used as the second block.

The block copolymers of this invention may be prepared by preparing the individual polymers which make up the blocks and then copolymerizing these polymers to form a block or graft copolymer. Alternatively, a polymer having epsilon-caprolatone and 1,3 dioxane-2-one linkages may be prepared in a reactor and then the monomers needed to form the other block or blocks are added directly to the reactor to thereby form the block copolymer.

In forming the block copolymers of this invention, the A (predominantly glycolide) block may be present in an amount from about 40 to about 75 percent by weight based on the weight of the final block copolymer. The B (random copolymer) block may be present in an amount from about 30 to about 50 weight percent based on the weight of the final block copolymer. Preferably, the A block comprises between about 50 and about 70 weight percent of the block copolymer. In a particularly useful embodiment, the A block comprises about 60 weight percent and the B block comprises about 40 weight percent of the final block copolymer. The copolymers of the present invention have a molecular weight such that their inherent viscosity is from about 0.8 to about 2.5 dl/g, and preferably from about 1.3 to about 1.8 dl/g measured at 30° C. at a concentration of 0.25 g/dl in hexafluoroisopranol (HFIP).

Each A and B block may comprise a single type of recurring monomeric unit. Alternatively, each block may comprise more than one type of recurring monomeric unit randomly distributed throughout each block. The block copolymers of the present invention may have repeating block units such as AB, ABA, ABAB, ABABA, BABA, etc.; with ABA being preferred.

The block copolymers of this invention can be formed into surgical articles using any know technique, such as, for example, extrusion, molding and/or solvent casting. The copolymers can be used alone, blended with other absorbable compositions, or in combination with non-absorbable components. A wide variety of surgical articles can be manufactured from the copolymer of the present invention. These include but are not limited to clips and other fasteners, staples, sutures, pins, screws, prosthetic devices, wound dressings, drug delivery devices, anastomosis rings, and other implantable devices. Fibers made from the copolymers of this invention can be knitted or woven with other fibers, either absorbable or nonabsorbable to form meshes or fabrics. The compositions of this invention can also be used as an absorbable coating for surgical devices. Preferably, however, the copolymers are spun into fibers to be used as sutures, either monofilament or multifilament.

Multifilament sutures of the present invention may be made by methods known in the art. Braid constructions such as those disclosed and claimed in U.S. Pat. Nos. 5,059,213 and 5,019,093 are suitable for the multifilament suture of the present invention.

A suitable process for the manufacture of monofilament sutures of the present invention comprises the operations of melt extruding the resin at an extrusion temperature of from about 180° C. to about 245° C. to provide a monofilament, stretching the solidified monofilament at a temperature of from about 30° C. to about 95° C. in water (or other suitable liquid medium) or at from about 30° C. to about 120° C. in air (or other suitable gaseous medium) at a stretch ratio of from about 3:1 to about 10:1 to provide a stretched monofilament. Optionally, the solidified monofilament may be stretched in air or other suitable gaseous medium preferrably at about 45° C. Preferably, the monofilament is then frozen at a temperature of from about −15° C. to about 0° C. The suture may then be annealed at a temperature of from about 80° C. to about 130° C. to provide the finished suture.

FIG. 1A schematically illustrates a monofilament suture manufacturing operation which is especially suitable for producing larger size sutures, e.g., those of sizes 2/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins of the present invention are introduced to the extruder through hopper 12. Any of the block copolymers of the present invention which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 2 to about 50 cm and preferably from about 1 to about 20 cm. If desired, a chimney (not shown), or shield, can be provided to isolate monofilament 16 from contact with air currents which might otherwise affect the cooling of the monofilament in an unpredictable manner. In general, barrel zone A of the extruder can be maintained at a temperature of from about 180° C. to 230° C., zone B at from about 190° C. to 240° C. and zone C at from about 200° C. to about 250° C. Additional temperature parameters include: metering pump block 13 at from about 190° C. to about 240° C., spin pack 14 at from about 200° C. to about 240° C., spinneret 15 at from about 190° C. to about 240° C. and quench bath at from about 10° C. to about 80° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament is wrapped around a first godet 21 provided with nip roll 22 to prevent slippage which might otherwise result from the subsequent stretching operation; and subsequently wrapped around godets 101, 102, 103 and 104 or any other suitable godet arrangement. Monofilament 16 passing from godet 104 is stretched, e.g., with stretch ratios on the order of from about 3:1 to about 10:1 and preferably from about 4:1 to about 7:1, to effect its orientation and thereby increase its tensile strength.

In the stretching operation shown in FIG. 1A, generally suitable for larger size sutures, e.g., sizes 2 to 2/0, monofilament 16 is drawn through hot water (or other suitable liquid medium) draw bath 23 by means of godets 24, 105, 106, 107 and 108 or any other suitable arrangement of godets which rotate at a higher speed than godet 104 to provide the desired stretch ratio. The temperature of hot water draw bath 23 is advantageously from about 30° C. to about 95° C. and preferably is from about 40° C. to about 60° C.

In the alternative stretching operation shown in FIG. 1B, generally preferred for smaller sutures sizes, e.g., sizes 3/0 to 9/0, monofilament 16 is drawn by godets 24, 105, 106, 107, and 108 or any other suitable godet arrangement through hot air convection oven chamber 23' at a temperature of from about 30° C. to about 120° C. and preferably from about 40° C. to about 70° C. to provide the desired amount of stretch. Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 26, 109,110, 111, and 112 or any other suitable godet arrangement through second hot air oven chamber 25 at a temperature of from about 30° C. to about 120° C. and preferably from about 40° C. to about 60° C. During the relaxation process, at these temperatures, monofilament 16 will generally recover to within about 80 to about 97 percent, and preferably to within about 95 percent, of its pre-annealed length to provide the finished suture. For relaxation, the third godet rotates at a slower speed than the second godet thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 80° C. to about 130° C., as described in U.S. Pat. No. 3,630,205. After a suitable period of residency in the heating cabinet, e.g., about 18 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air or nitrogen type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

The suture of the present invention, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this invention to incorporate one or more medico-surgically useful substances into the present invention, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures of the present invention in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion.

In order that those skilled in the art may be better able to practice the present invention, the following examples are given as an illustration of the preparation of block copolymer of the present invention as well as of the preparation and superior characteristics of the sutures of the present invention. It should be noted that the invention is not limited to the specific details embodied in the examples and further that all ratios or parts recited are by weight.

EXAMPLE 1

1,3 dioxane-2-one (1090 grams) and epsilon-caprolactone (660 grams) are added to a reactor along with 1.0 grams of stannous octoate and 1 gram of diethylene glycol. The mixture is heated and placed at 160° C., with stirring under a nitrogen atmosphere for 3.5 hours. The epsilone-caprolactone/1,3 dioxane-2-one copolymer is then sampled.

Five hundred grams of dry glycolide are then added to the reactor. The setting for the temperature of the reactor is then increased to 210° C. When the temperature of the reactor reaches 195° C., 2750 grams of glycolide are added with continued stirring. The polymerization is continued for about 25 minutes at 210° C.

The reaction product is isolated, comminuted, and treated to remove residual reactants using known techniques. The copolymer is then heated under vacuum to remove residual water, residual solvent, and/or unreacted monomer.

EXAMPLE 2

1,3 dioxane-2-one (1249 grams) and caprolactone (751 grams) are added to a reactor along with 1.0 grams of stannous octoate and 1 gram of diethylene glycol. The mixture is heated and placed at 160° C. (with stirring) under a nitrogen atmosphere for 3.5 hours. The capralactone/1,3 dioxane-2-one copolymer is then sampled.

Five hundred grams of dry glycolide are then added to the reactor. The setting for the temperature of the reactor is then increased to 210° C. When the temperature of the reactor reaches 195° C., 2500 grams of glycolide are added with continued stirring. The polymerization is continued for about 20 minutes at 210° C.

The reaction product is isolated comminuted, and treated to remove residual reactants using known techniques. The copolymer is then heated under vacuum to remove residual water, residual solvent and/or unreacted mononer.

Table I below sets forth typical conditions for extruding, stretching monofilament sutures in accordance with this invention. All of the monofilament sutures were fabricated from the resin of Example 1 and Example 2.

TABLE I
CONDITIONS OF MANUFACTURING OF MONOFILAMENT SUTURES OF THE PRESENT INVENTION

| Process Conditions | Example 1 | Example 2 |
|---|---|---|
| | Extrusion | Operation |
| extruder screw, rpm | 1.5 | 2.4 |
| pump, rpm | 6.9 | 15.4 |
| barrel temp., °C., zone A | 200 | 195 |
| barrel temp., °C., zone B | 222 | 220 |
| barrel temp., °C., zone C | 223 | 223 |
| clamp temp., °C., | 223 | 225 |
| adapter temp., °C. | 226 | 225 |
| pump temp., °C. | 224 | 225 |
| block temp., °C. | 224 | 225 |
| barrel melt temp., °C. | 218 | 219 |
| pump melt temp., °C. | 217 | 220 |
| spinneret melt temp., °C. | 217 | 218 |
| barrel pressure, psi | 790 | 800 |
| pump pressure, psi | 500 | 500 |
| spinneret pressure, psi | 1050 | 500 |
| pump size, cc per revolution | 0.297 | 0.160 |
| diameter of spinneret, orifices, mm | 1.25 | 1.25 |
| no. of spinneret orifices | 1 | 1 |
| quench bath temp., °C. | 18 | 18 |
| Stretching (Orienting) Operation | | |
| draw oven temp., °C. | 75 | 43 |
| first godet, mpm | 4.6 | 6.9 |
| second godet, mpm | 23.2 | 33.8 |
| second oven temp, °C. | 100 | 52 |
| third godet, mpm | 28.8 | 36.6 |
| draw ratio | 6.3:1 | 5.3:1 |
| Freezing Operation | | |
| temp., °C. | −13 | −13 |
| time (hrs.) | 18 | 18 |
| Annealing Operation | | |
| oven temp., °C. | 97 | 85 |
| time (hrs.) | 18 | 18 |
| shrinkage (%) | 10 | 10 |

The physical properties of the sutures and the procedures employed for their measurement are set forth in Table II as follows:

TABLE II
PROCEDURES FOR MEASURING PHYSICAL PROPERTIES OF MONOFILAMENT SUTURES OF THE PRESENT INVENTION

| Physical Property | Test Procedure |
|---|---|
| knot-pull strength, kg | U.S.P. XXI, tensile strength, sutures (881) |
| straight-pull strength, kg | ASTM D2256-88, Instron Corporation |
| elongation, % | ASTM D2256-88 |
| tensile strength, kg/mm$^2$ | ASTM D2256-88, Instron Corporation Series IX Automated Materials Testing System 1.03A |

Table III below sets forth the physical properties of the suture of the present invention.

TABLE III

| Physical Property | Example 1 | Example 2 |
|---|---|---|
| diameter (mm) | 0.301 | 0.304 |
| knot-pull strength (kg) | 2.3 | 2.0 |
| Straight-pull strength (kg) | 2.8 | 2.5 |
| Elongation (%) | 21 | 21 |
| Tensile Strength (kg/mm$^2$) | 39 | 33 |

As the data in Table III illustrates, the suture made of the copolymer of the present invention showed acceptable physical properties, such as knot pull and straight-pull strength.

Obviously, other modifications and variations of the present invention are possible in light of the above teachings. It is therefore to be understood that changes may be made in particular embodiments of the invention described which are within the full intended scope of the invention as described by the claims.

What is claimed is:

1. A block copolymer comprising:
  a) from about 50 to about 65 percent by weight of copolymer blocks comprising a predominant amount of glycolic acid ester units; and
  b) the remainder of said blocks comprising random copolymers of caprolactone and 1,3 dioxane-2-one, said blocks comprising random copolymers of epsilon-caprolactone and 1,3 dioxane-2-one being formed from the random polymerization of about 35 percent by weight of caprolactone and about 65 percent by weight 1,3 dioxane-2-one.

2. The block copolymer of claim 1, wherein said block copolymer is a tri-block copolymer.

3. The tri-block copolymer of claim 2, comprising:
  a) about 50 to about 65 percent of said copolymer by weight end blocks, said end blocks comprising a predominant amount of glycolic acid ester units, and
  b) a center block comprising random copolymers of epsilon-caprolactone and 1,3 dioxane-2-one.

4. A surgical article formed totally or in part from the block copolymer of claim 1.

5. The surgical article of claim 4, wherein said surgical article is selected from the group consisting of clips, staples, sutures, pins, screws, prosthetic devices, anastomosis rings, and growth matrices.

6. The surgical article of claim 5, wherein said suture is a monofilament suture.

7. The surgical article of claim 4 further comprising a medico-surgically useful substance.

8. A block copolymer comprising:

a) from about 40 to about 70 percent by weight of said copolymer blocks comprising a predominant amount of glycolic acid ester units; and b) the remainder of said blocks comprising random copolymers of caprolactone and 1,3 dioxane-2-one, said blocks comprising random copolymers of epsilon-caprolactone and 1,3 dioxane-2-one formed from the random polymerization of caprolactone and 1,3 dioxane-2-one.

9. The block copolymer of claim 8, wherein said block copolymer is a tri-block copolymer.

10. A surgical article formed totally or in part from the block copolymer of claim 8.

11. The surgical article of claim 10, wherein said surgical article is selected from the group consisting of clips, staples, sutures, pins, screws, prosthetic devices, anastomosis rings, and growth matrices.

* * * * *